Patent Number: 5,095,093
Date of Patent: Mar. 10, 1992

[54] PROTECTIVE FOUR AMINO ACID EPITOPE AGAINST *PLASMODIUM VIVAX* MALARIA

[75] Inventors: Stephen L. Hoffman, Gaithersburg; Yupin Charoenvit, Silver Spring, both of Md.; Trevor R. Jones, Brooklyn, Conn.

[73] Assignee: The United States of America as represented by the Secretary of the Navy, Washington, D.C.

[21] Appl. No.: 609,551

[22] Filed: Nov. 6, 1990

[51] Int. Cl.$^5$ ............................................. A61K 37/00
[52] U.S. Cl. ..................................... 530/330; 514/895
[58] Field of Search ........................... 514/18, 19, 895; 530/330

[56] References Cited

U.S. PATENT DOCUMENTS 4,466,917 8/1984 Nussenzweig et al. .
4,693,994 9/1987 McCutchan et al. .
4,707,357 11/1987 Dame et al. .
4,826,957 5/1989 Nussenzweig et al. .
4,957,869 9/1990 Arnot et al. .

OTHER PUBLICATIONS

Collins et al., Am. J. Trop. Med. Hyg., 40(5), 1989, pp. 455–464.
Fundamental Immunology, William E. Paul, ed., pp. 975–977 (1989).

*Primary Examiner*—Lester L. Lee
*Assistant Examiner*—E. J. Kraus
*Attorney, Agent, or Firm*—A. David Spevack; William C. Garvert; Thomas E. McDonnell

[57] ABSTRACT

A synthetic peptide of the human malaria *Plasmodium vivax*, containing at least one repeat of a synthetic peptide having the amino acid sequence Ala-Gly-Asp-Arg (AGDR) which is a protective epitope found on the circumsporozoite (CS) protein of the sporozoites of the human maleria *Plasmodium vivax*. When a monoclonal antibody specific for this four amino acid sequence binds to the CS protein of the *P. vivax* sporozoite in vivo, infection is prevented. Also described are pharmaceutical formulations of these peptides.

4 Claims, No Drawings

SEQUENCE LISTING (1) GENERAL INFORMATION:

(i) APPLICANT: Hoffman, Stephen L.
              Charoenvit, Yupin
              Jones, Trevor R.

(ii) TITLE OF INVENTION: PROTECTIVE FOUR AMINO ACID EPITOPE
         AGAINST PLASMODIUM VIVAX MALARIA (iii) NUMBER OF SEQUENCES: 1

(iv) CORRESPONDENCE ADDRESS:
        (A) ADDRESSEE: Naval Medical Res. & Dev. Cmd.
        (B) STREET: National Naval Medical Center
        (C) CITY: Bethesda
        (D) STATE: Maryland
        (E) COUNTRY: USA
        (F) ZIP: 20889-5044

(v) COMPUTER READABLE FORM:
        (A) MEDIUM TYPE: Floppy disk
        (B) COMPUTER: IBM PC compatible
        (C) OPERATING SYSTEM: PC-DOS/MS-DOS
        (D) SOFTWARE: PatentIn Release #1.0, Version #1.25

(vi) CURRENT APPLICATION DATA:
        (A) APPLICATION NUMBER: US 07/609,551
        (B) FILING DATE: 06-NOV-1990
        (C) CLASSIFICATION:

(viii) ATTORNEY/AGENT INFORMATION:
        (A) NAME: Spevack, A. David
        (B) REGISTRATION NUMBER: 24,743
        (C) REFERENCE/DOCKET NUMBER: N.C. 72,634

(ix) TELECOMMUNICATION INFORMATION:
        (A) TELEPHONE: (301) 295-6759
        (B) TELEFAX: (301) 295-4033

(2) INFORMATION FOR SEQ ID NO:1:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Plasmodium vivax
        (B) STRAIN: sal-1
        (C) INDIVIDUAL ISOLATE: none
        (D) DEVELOPMENTAL STAGE: Sporozoite (xi) SEQUENCE DESCRIPTION: SEQ ID NO:1:

Ala Gly Asp Arg

PROTECTIVE FOUR AMINO ACID EPITOPE AGAINST *PLASMODIUM VIVAX* MALARIA

BACKGROUND OF THE INVENTION

1. Field of the Invention

This invention relates to a synthetic peptide of the human malaria *Plasmodium vivax*, more particularly the invention relates to a synthetic or recombinant peptide containing the sequence AGDR which is a protective epitope found on the circumsporozoite (CS) protein of the sporozoites of the human malaria *Plasmodium vivax*. When a monoclonal antibody specific for this four amino acid sequence binds to the CS protein of the *P. vivax* sporozoite in vivo, infection is prevented.

2. Description of the Prior Art

Of the four human malarias, *P. vivax* and *P. falciparum* are the most common and cause the majority of the malaria-induced disease seen worldwide. Prevention of infection by these human parasites would alleviate a major health problem in the tropical and subtropical areas of the world. The most promising method for the control of malaria appears to be the development and use of vaccines. One approach to malaria vaccine development involves the use of the CS protein as a vaccine antigen. This protein covers the surface of the sporozoite. The sporozoite is the life stage of the parasite which is transmitted to humans by feeding female Anopheline mosquitoes. Evidence from both mouse and human malarias indicates that antibodies to the CS protein can provide protection in vivo against infection by sporozoites (Charoenvit et al., Infect. Immunity 55: 604, 1987; Charoenvit et al., in press, J. Immun. 1991; Charoenvit et al., in press, Science 1990).

In 1985, McCutchan and colleagues sequenced the gene for the CS protein in *P. vivax* and determined the amino acid sequence derived from the gene (McCutchan et al., Science 230: 1381, 1985). In 1987, McCutchan and Wistar, in U.S. Pat. No. 4,693,994, described a repeated nine amino acid sequence within the CS protein as an immunodominant synthetic peptide. The repeated sequence is Gly-Asp-Arg-Ala-Asp-Gly-Gln-Pro-Ala. In the '994 patent and in other publications, McCutchan/Wistar maintain that the nine amino acid sequence is capable of inducing antibodies protective against *P. vivax* malaria. Experimental evidence indicates that while the McCutchan/Wistar sequence stimulates the development of anti-CS antibody in humans, it is not capable of inducing protective antibodies. In an article published in Am. J. Trop. Med. Hyg. 40(5), p 455-464 (1989), Collins et al. describes tests in which Saimiri monkeys (*Saimiri sciureus boliviensis*), which are susceptible to human vivax malaria, were immunized with two different preparations (VIVAX-1 and $NS1_{81}V20$). Both preparations contain the McCutchan/Wistar peptide (Gly-Asp-Arg-Ala-Asp-Gly-Gln-Pro-Ala). When these monkeys were challenged with $10^4$ *P. vivax* sporozoites, there was no significant protection.

Nussenzweig et al., in U.S. Pat. No. 4,826,957, describes an immunogenic recombinant yeast expression product which contains a long sequence incorporating a portion of the *P. vivax* circumsporozite. The sequence contains multiple repeats of the sequence Gly-Asp-Arg-Ala-Asp-Gly-Gln-Pro-Ala as part of a complex polypeptide. The vaccine causes the formation of antibodies, to Gly-Asp-Arg-Ala-Asp-Gly-Gln-Pro-Ala, but does not provide consistent protection against challenge with malaria sporozoites. There is a need for a simple material to generate a vaccine against *P. vivax*.

SUMMARY OF THE INVENTION

Accordingly, it is an object of this invention to characterize the nature of a protective epitope found within the amino acid sequence of the CS protein of *P. vivax*.

It is a further object of the present invention to provide a synthetic peptide which will form the basis of a synthetic vaccine capable of inducing antibodies protective against infection caused by the sporozoites of *P. vivax*.

Another object of the invention is an immunogenic peptide incorporated in an antimalarial vaccine preparation.

An additional object of the invention is a method of causing the formation of antibodies which will immunize against malaria caused by *P. vivax*.

Yet another object of the invention is a vaccine protective against malaria caused by *P. vivax*.

Other objects and advantages of this invention will become clear as the detailed description of the present invention is presented.

These and additional objects of the invention are accomplished by at least one repeat of a synthetic peptide having the amino acid sequence Ala-Gly-Asp-Arg (AGDR) and pharmaceutical formulations of these peptides.

DESCRIPTION OF THE PREFERRED EMBODIMENTS

The monoclonal antibody originally used by McCutchan and colleagues (McCutchan et al., Science 230: 1381, 1985) to isolate the protein and the nucleotide sequence which later became the subject of the McCutchan/Wistar U.S. Pat. No. 4,693,994 was originally developed by Charoenvit and Beaudoin of the Infectious Diseases Department, Naval Medical Research Institute (NMRI). It was used at NMRI as a passive immunization agent. Saimiri monkeys were immunized by the intravenous infusion of 2 mg per animal of the monoclonal antibody (designated NVS3) then challenged with $10^4$ *P. vivax* sporozoites injected intravenously. Four of six animals were completely protected and the remaining two experienced a significant delay in the onset of disease. These findings are the subject of a concurrently filed application filed in the name of Charoenvit et al. and titled "NVS3 as a Passive Protective Agent Against *P. Vivax*." Analysis of this protective antibody by epitope scanning technology revealed that NVS3 has as its specific epitope the amino acid sequence alanine-glycine-aspartic acid-arginine (Ala-Gly-Asp-Arg, otherwise abbreviated as AGDR). Through subsequent work, it was surprising to find that circulating antibodies against the epitope AGDR protect against infection by *P. vivax* sporozoites and hence AGDR is immunogenic.

The analysis of serum samples from humans and Saimiri monkeys vaccinated with a vaccine, $NS1_{81}V20$, containing the McCutchan/Wistar sequence (Gly-Asp-Arg-Ala-Asp-Gly-Gln-Pro-Ala, also abbreviated as GDRADGQPA), which contains the amino acids Alanine, Glycine, Aspartic acid, and Arginine, revealed that both the humans and monkeys generated antibodies that bound to *P. vivax* sporozoites and to the McCutchan/Wistar sequence, but no antibodies could be detected to the protective epitope AGDR. As noted by Collins et al., this vaccine did not produce statistically significant protection against *P. vivax* malaria. This lack of protection is surprising because Alanine is the last acid in the McCutchan/Wistar sequence and Glycine, Aspartic acid and Arginine are the first acids in the series of the McCutchan/Wistar sequence, therefore the McCutchan/Wistar sequence contains the AGDR sequence when there is more than one repeat, and the vaccine NS1$_{81}$V20 contained multiple copies of AGDR.

The present invention rests on the discovery of an amino acid sequence within the CS protein which is the epitope of monoclonal antibodies which protect against sporozoite-induced *P. vivax* malaria. The knowledge that this amino acid sequence is the epitope of an antibody which prevents infection with *P. vivax* malaria, allows the design of synthetic or recombinant proteins based on this amino acid sequence which can be used as vaccines.

Failure of vaccines already containing the protect epitope AGDR to induce a protective antibody response indicates that the presentation of AGDR-based vaccines is important. These vaccines should not contain the extraneous amino acids from the McCutchan/Wistar sequence. The simplest embodiment of the invention is the peptide AGDR. In another embodiment the AGDR sequence is a simple chains of repeating AGDR sequences. The exact number of repeats is not critical. Up to about thirty repeats is preferred. In yet another embodiment, the peptide for the vaccine is formed as simple chains containing AGDR sequences separated by spacer sequences. Again, the number of repeats or the number of spacers is not critical except that care must be taken to avoid creating the hindrances which must be present in the McCutchan/Wistar sequence. The spacers can separate single or multiple repeats of the AGDR sequence. MAPS (multiple antigenic peptide systems) can be formed by conjugating multiple AGDR containing chains to a central moiety. These MAPS are described by Tam et al., PNAS USA 86: 9084, 1989. Combinations of these several forms are considered part of the invention.

To be used as vaccines, these AGDR-based peptides can be linked to a carrier protein which may or may not contain a T-cell epitope which may or may not be of malarial origin. This peptide/carrier combination then may be delivered in conjunction with delivery systems and adjuvants including but not exclusive of aluminum hydroxide, liposomes, monophosphoryl lipid A and Mycobacterium components.

It is noted that those technical terms of phrases used here which have not been specifically defined have the same meaning as generally understood by one of ordinary skill in the art to which this invention belongs. The term "synthetic" as used here is intended to indicate that the Cs protein from *P. vivax* occurring in its natural state is specifically excluded from this invention. "Synthetic", as used here, is not intended to preclude production of AGDR-based vaccines by biological methods including, for example, chemical synthetic and DNA recombinant techniques.

Having described the invention, the following examples are given to illustrate specific applications of the invention including the best mode now known to perform the invention. These specific examples are not intended to limit the scope of the invention described in this application.

EXAMPLE 1

The AGDR-based molecules of this invention are produced by chemical synthesis, using the peptide synthesis technology based on, but not limited to that developed by Merrifield (Merrifield, *J. Amer. Chem. Soc.* 85: 2149, 1963). In the present invention, the synthesis is initiated by condensing the first amino acid onto a solid matrix by an esterification reaction between the activated carboxyl group of the amino acid and the linker attached to the solid matrix. This step is performed in an aliphatic solvent such as N,N-dimethylformamide (DMF). The α-amino groups of all amino acids used in this synthesis are protected by either tert-butyl-oxy-carbonyl (t-Boc) or fluorenyl-methyl-oxy-carbonyl (Fmoc) groups. Fmoc chemistry is preferred. This protective group is removed, in the case of Fmoc chemistry, by treatment with a 20% piperidine solution in DMF. After deprotection, the next amino acid is added. This is accomplished by condensing the second amino acid onto the first by means of an acylation reaction between the acid group on the first amino acid and the deprotected α-amino group on the second amino acid in an inert organic solvent, such as DMF, and in the presence of with a catalyst, such as 1-hydroxybenzotriazole (HOBT). These reactions are carried out at room temperature. Any of the amino acids can be added in any sequence desired. In this invention, the amino acids were added in such an order to create the peptide AGDR.

The completed peptide is removed from the matrix by known techniques of acid hydrolysis; in this invention, hydrofluoric acid was used. Once hydrolysed free of the matrix, the matrix is filtered out, the peptides repeatedly washed in water and then concentrated to dryness, redissolved in water and freeze-dried. This peptide was then purified by dissolving it in water and subjecting it to gel filtration chromatography over a Sephedex G-25 resin eluted with 0.1M CH$_3$COOH. The major peak was collected and freeze-dried.

EXAMPLE 2

Many vaccines based on the tetrapeptide AGDR can be synthesized. This includes but are not limited to single AGDR molecules, straight chains of repeating AGDR sequences such as (AGDR)$_3$ and (AGDR)$_6$, and branched chain polymers consisting of (AGDR)$_3$ and (AGDR)$_3$ plus a known T-cell helper site. The helper T-cell peptide may be, but is not restricted to, the sequence EYLDKVRATVGTEWTPCSVT. These branched chain vaccines are known as MAPS (multiple antigen peptide systems). The basic peptide chains are synthesized according to Example 1. The synthesis of branched chains and the combination of chains containing two different epitopes is accomplished in accordance with the procedures described by Tam and Lu (Tam et al., PNAS, 86: 9084, 1989).

EXAMPLE 3

The present invention can be delivered by injection or other known means to subjects in a variety of ways. Some of these techniques and dosage ranges are described in U.S. Pat. Nos. 4,693,994 and 466,917. For administration, they may be coupled to carrier proteins including but not restricted to tetanus toxoid and cholera toxin. The above described molecules can be absorbed to alum (aluminum hydroxide) and delivered parenterally in an aqueous solution. They can also be solubilized in other adjuvants including but not restricted to liposomes, squalane and monophosphoryl lipid A and may also contain immunopotentiators such as bacterial cell wall and cytoskeleton.

EXAMPLE 4

The 8-residue peptide (AGDR)$_2$ is synthesized by the stepwise solid-phase method of Merrifield. R. B.: Solid phase peptide synthesis. I. The synthesis of a tetrapeptide; *J. Am. Chem. Soc.*; 85: 2149-2154; 1963. Pam-t-Boc-L-arginine (Tos) resin (0.5 nmole) is used as the starting point of the synthesis. The protected peptide resin is deprotected by hydrogen fluoride/p-cresol (9:1, v/v for 1 hour at 0° C.).

Obviously, many modifications and variations of the present invention are possible in light of the above teachings. It is therefore to be understood that, within the scope of the appended claims, the invention may be practiced otherwise than as specifically described.

What we claim is:

1. A synthetic peptide having at least one unhindered repeat of the amino acid sequence alanine-glycine-aspartic acid-arginine (ala-gly-asp-arg also designated AGDR) as the only immunogenic active site.

2. The synthetic peptide according to claim 1 comprising only one repeat of the sequence alanine-glycine-aspartic acid-arginine (AGDR).

3. The synthetic peptide according to claim 1 having multiple tandem repeats of the amino acid sequence alanine-glycine-aspartic acid-arginine.

4. The synthetic peptide according to claim 1 wherein each repeat of the sequence alanine-glycine-aspartic acid-arginine is separated by an inert, non-hindering spacer.

* * * * *